United States Patent [19]

Lapeyre et al.

[11] Patent Number: 5,089,018

[45] Date of Patent: Feb. 18, 1992

[54] TOTAL HEAT PROSTHESIS

[75] Inventors: Didier Lapeyre, Chaignes, 27120 Pacy-sur-Eure; René Veragen, Chatou, both of France

[73] Assignee: Didier Lapeyre, Pacy-sur-Eure, France

[21] Appl. No.: 264,951

[22] PCT Filed: Jan. 27, 1988

[86] PCT No.: PCT/FR88/00043

§ 371 Date: Nov. 28, 1988

§ 102(e) Date: Nov. 28, 1988

[87] PCT Pub. No.: WO88/05313

PCT Pub. Date: Jul. 28, 1988

[30] Foreign Application Priority Data

Jan. 27, 1987 [FR] France .............................. 87 000908

[51] Int. Cl.⁵ .............................................. A61M 1/10
[52] U.S. Cl. ............................................ 623/3; 600/16
[58] Field of Search ........................ 623/3; 600/16, 17

[56] References Cited

U.S. PATENT DOCUMENTS

| | | | |
|---|---|---|---|
| 4,222,127 | 9/1980 | Donachy et al. | 623/3 |
| 4,427,470 | 1/1984 | Kolff | 623/3 |
| 4,506,658 | 3/1985 | Casile | 623/3 |
| 4,573,997 | 3/1986 | Wisman et al. | 623/3 |
| 4,588,404 | 5/1986 | Lapeyre | 623/3 |
| 4,652,265 | 3/1987 | McDougall | 623/3 |
| 4,781,715 | 11/1988 | Wurzel | 623/3 |
| 4,781,716 | 11/1988 | Richelsoph | 623/3 |

Primary Examiner—Randy C. Shay
Attorney, Agent, or Firm—Oblon, Spivak, McClelland, Maier & Neustadt

[57] ABSTRACT

Total heart prosthesis including a casing implantable in the pericardial cavity, the geometry of which is similar to that of the natural heart, with a motor device inside the casing which essentially includes two membranes, one of which works during the elongation stroke within a space defining the right ventricle and the other of which works during the deformation stroke within a space defining the left ventricle. Blood bags are enclosed within the right and left ventricular spaces adapted to be connected to vessels of the circulatory system of a patient. The membrane of the right ventricle and a support associated therewith are mounted within the prosthesis casing such that the movement of the membrane during the elongation stroke (systole) is broken down into two phases, one of which is a displacement without elongation and the other, only, is accompanied with an elongation. Movement of the membrane during relaxation (diastole) includes first a retraction phase followed by a displacement without modification of the shape of the membrane and of the support associated therewith.

11 Claims, 4 Drawing Sheets

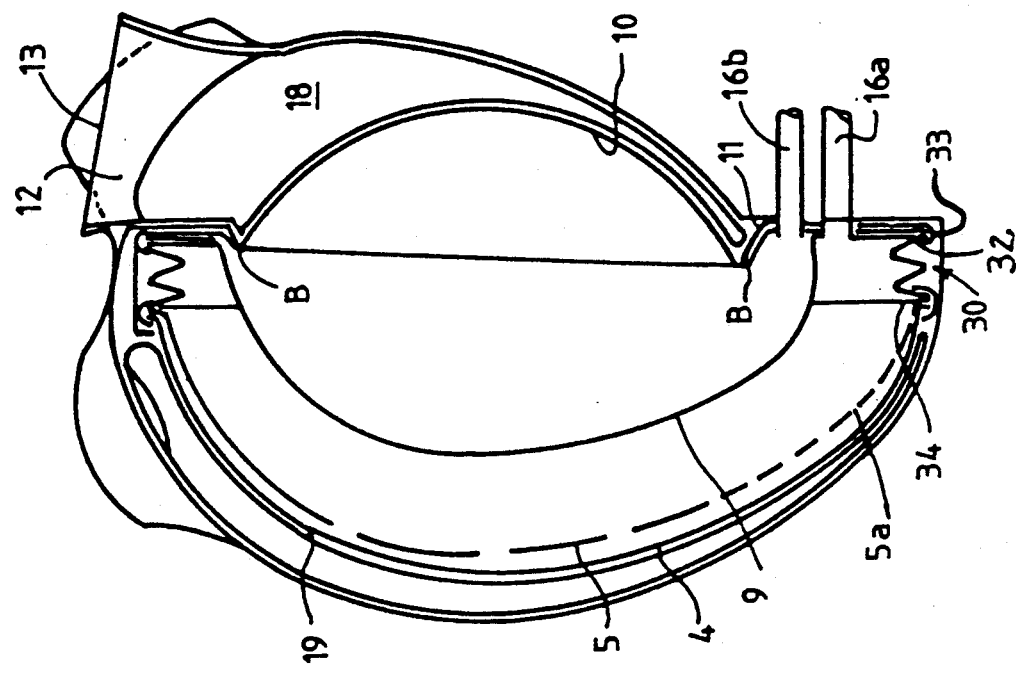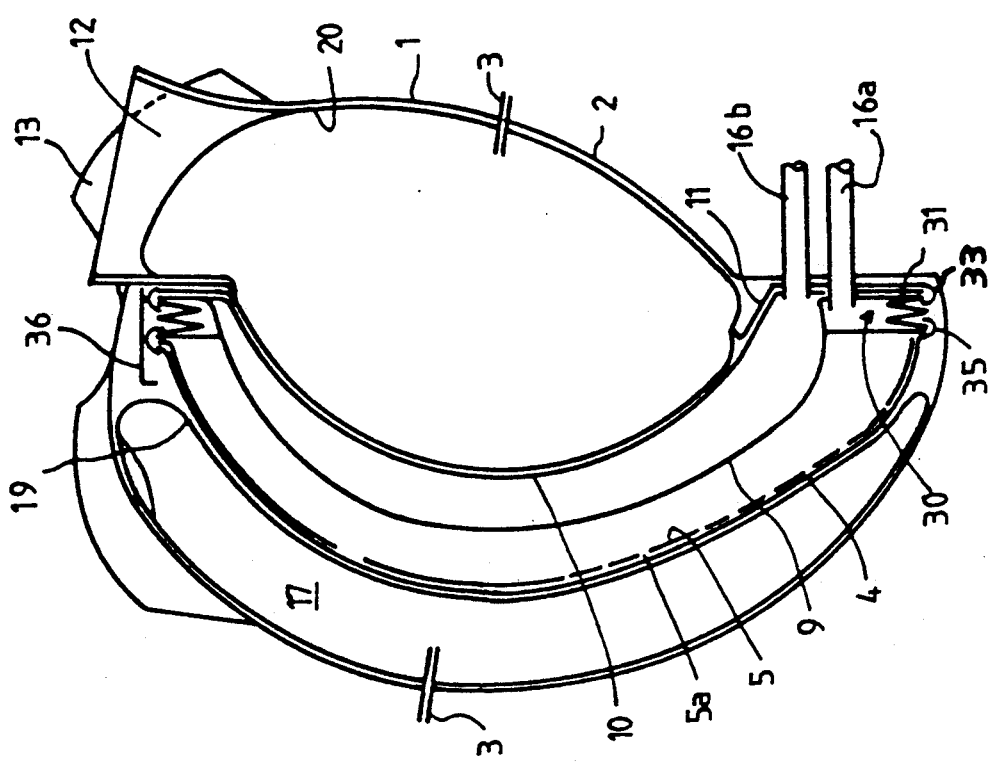

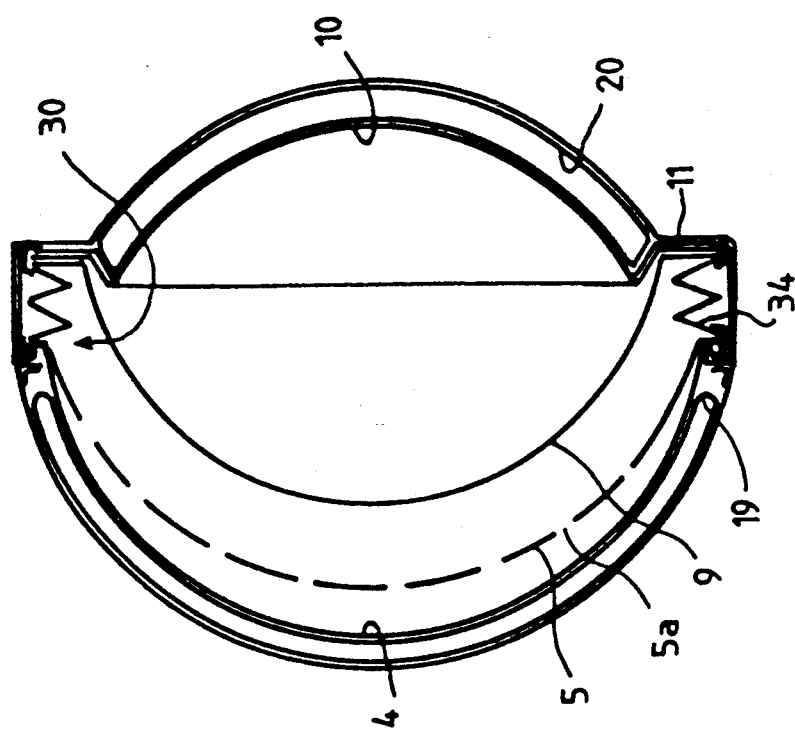
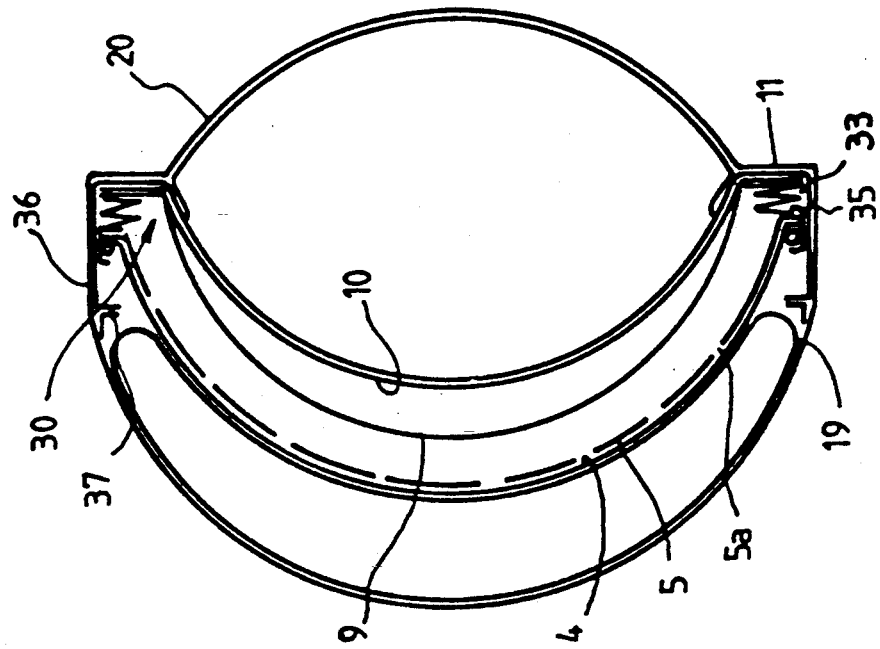

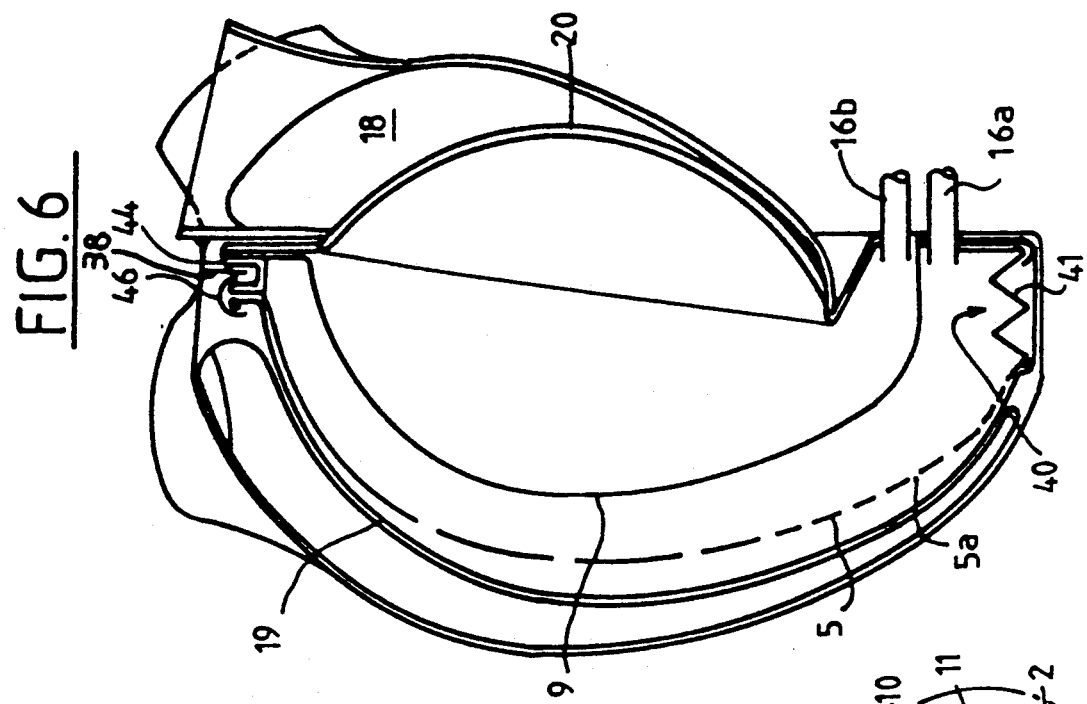
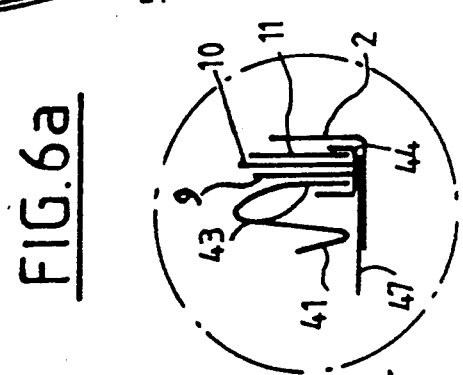
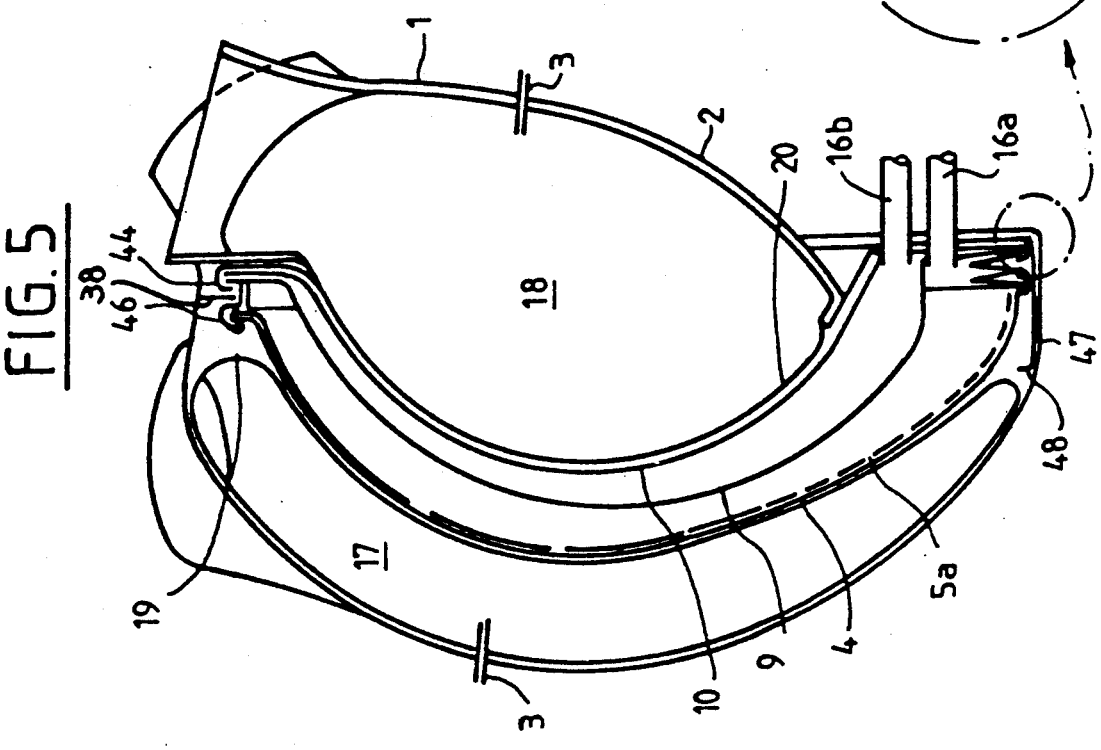

5,089,018

TOTAL HEAT PROSTHESIS

BACKGROUND OF THE INVENTION

1. Field of the Invention

The invention relates to an improved total heart prosthesis.

It relates more particularly to a small size total heart prosthesis with a single activation source for the right and left ventricles, having a functional geometry which is a close as possible to the functional geometry of the natural heart and which reproduces the hemodynamic functioning laws of the natural heart, in particularly STARLING'S law and SARNOFF'S law.

2. Discussion of the Background

A prosthesis of this type which has shown itself to be satisfactory in operation, not only during tests in vitro but also tests in vivo on animals is divulged in FR-A-2 446 631. It comprises a case implantable in the pericardial cavity and the geometry of which is very similar to the geometry of a natural heart with, inside this case, a motor device essentially formed by two membranes one of which works during the elongation stroke within a space defining the right ventricle and the other of which works during the deformation stroke within a space defining the left ventricle, the motor device acting respectively on blood bags enclosed in the right and left ventricular spaces. The blood bags are adapted to be connected to the vessels of the circulatory system of a patient by means of valves mounted in valvular orifices formed in the case of the prosthesis, the latter being actuated by means activating the motor device such as an extra-corporeal pneumatic energy source or an electric motor with implantable battery or an electric motor controlled by a nuclear energy source etc., with servo loop means for regulating the blood flow.

As described in the above patent, the membrane of the right ventricle of the prosthesis, with which a support is associated, is an elastomer material membrane subjected to alternate elongations during a very large number of elongation-deformation cycles so that, after several tens of millions of alternating movements, alterations may appear such as micro-cracks which, in the long run, may cause its destruction.

Therefore the problem arises of providing a total heart prosthesis of the above described type, in which the membrane of the right ventricle has a lifespan as long as possible, in any case greater than two hundred and fifty million cycles and which, however, satisfies the other conditions imposed on the motor device of the prosthesis, in particular ensuring for each pulsation the ejection of a volume between 60 and 90 ml of blood. Considering, on the one hand, that for a membrane having a certain area, this useful volume is directly related to the elongation of the membrane and that, on the other hand, the maximum elongation conditions the number of cycles to which said membrane may be subjected without the appearance of micro-cracks, the problem which arises is then that of providing in the motor device of the prosthesis a membrane arrangement ensuring the desired volume variation for an elongation as small as possible.

SUMMARY OF THE INVENTION

This problem is solved, in accordance with the invention, by the fact that the elastic membrane of the right ventricle and the support part which is associated therewith are mounted in the case of the prosthesis by means adapted so that the movement of said membrane during elongation (systole) is broken down into two phases, one of which is a displacement without elongation and the other, only, is accompanied by an elongation whereas the reverse movement (diastole) comprises first a retraction phase followed by a displacement without modification of the shape of said membrane and of the support part associated therewith.

With such an arrangement, the elongation of the membrane of the right ventricle of the motor device is limited to an elongation value less than 8 to 10% so that the fatigue forces are considerably reduced along with, accordingly, the maintenance of the integrity of the membrane for at least two hundred and fifty million operating cycles.

In one embodiment, the means for breaking the movement of the membrane of the right ventricle down into two phases comprise at least one bellows adapted to be connected to the pneumatic energy source and on which the membrane and the support part associated therewith are fixed.

In one embodiment, the bellows is of the parallel displacement type.

In a variant, the bellows is of the pendular displacement type.

In both embodiments, the invention provides for the bellows itself to be made from an elastic material and for its end, distant from that by which the membrane and the support part associated therewith are fixed, to be fixed by crimping to a sealed dividing wall separating the right and left ventricular spaces from the prosthesis. Also fixed to the dividing wall is the membrane working on deformation of the left ventricle.

According to another characteristic of the invention, the displacement phase without elongation of the membrane working on elongation of the right ventricle is limited, during elongation of said membrane (systole) by abutting against a stop member on the mobile end of the bellows to which said membrane and the support part associated therewith are fixed.

Such a contruction of the right ventricle makes it possible to reduce the drive power of the pneumatic energy source, with respect to that of the known prosthesis, because of the smaller amount of energy required for actuating the membrane of said ventricle, whose reverse return movement to its initial molded form (relaxation)—which is the one which corresponds to the systole beginning—is aided in a complementary manner by a slight pneumatic depression.

The presence of a dry or liquid lubricant between the blood bags, the case of the prosthesis, the membranes of the motor device and the means associated with the membrane of the right ventricle for breaking down the movement thereof into two distinct phases contributes to the correct operation of the prosthesis.

The general form of the case and that of the right and left ventricular spaces are close to those of the prosthesis described in the above mentioned French patent, so that said ventricular spaces having increasing dimensions from the tip towards the base of the prosthesis, promote a correct orientation of the speed vectors of the blood in movement towards the valvular outlet orifices without a stasis zone.

The pendular bellows embodiment further increases the desirable effect of the overall geometry of the prosthesis by the fact that it first causes the tip of the blood bag of the right ventricle to be emptied at a higher rate than the rest of the bag, because of the greater distance separating this tip from the articulation hinge of the pendular movement, without however modifying the speed of the blood at the valvular orifice, on the one hand and, on the other hand, continuation under the usual conditions of emptying the bag when, at the end of the first movement phase of the membrane of the right ventricle, the latter begins to work under elongation, only.

BRIEF DESCRIPTION OF THE DRAWINGS

The invention will be well understood from the following description, given by way of example with reference to the accompanying drawings in which:

FIG. 1 is a schematic view in longitudinal section of a total heart prosthesis in accordance with the invention;

FIG. 2 is a view similar to that of FIG. 1 for another condition of the motor device;

FIG. 3 is a schematic cross sectional view of the prosthesis in the condition shown in FIG. 1;

FIG. 4 is a cross sectional view of the prosthesis in the condition shown in FIG. 2;

FIG. 5 is a view similar to that of FIG. 1 but for another embodiment;

FIG. 6 is a view of this embodiment but in another condition of the motor device;

FIG. 6a is a detail view of the embodiments shown in FIGS. 1 to 4 and 5 and 6;

DESCRIPTION OF THE PREFERRED EMBODIMENTS

Referring first of all to FIGS. 1 and 2 relative to a first embodiment of a total heart prosthesis of the invention, the latter comprises a case made from a material which is non toxic with respect to the surrounding tissues, such as polyurethane, with an upper part and a lower part joined together sealingly by appropriate means, e.g. clips 3 placed in a plane perpendicular to the working directions of the motor device. The latter comprises a first membrane 4, made from an elastomer type material, which works under elongation and whose area is at least about 150 cm$^2$ for a prosthesis of a total size of about 125 mm but whose area may be of the order of at least 220 cm$^2$ for a larger sized prosthesis, e.g. having a total size of 150 mm.

Figure 9:
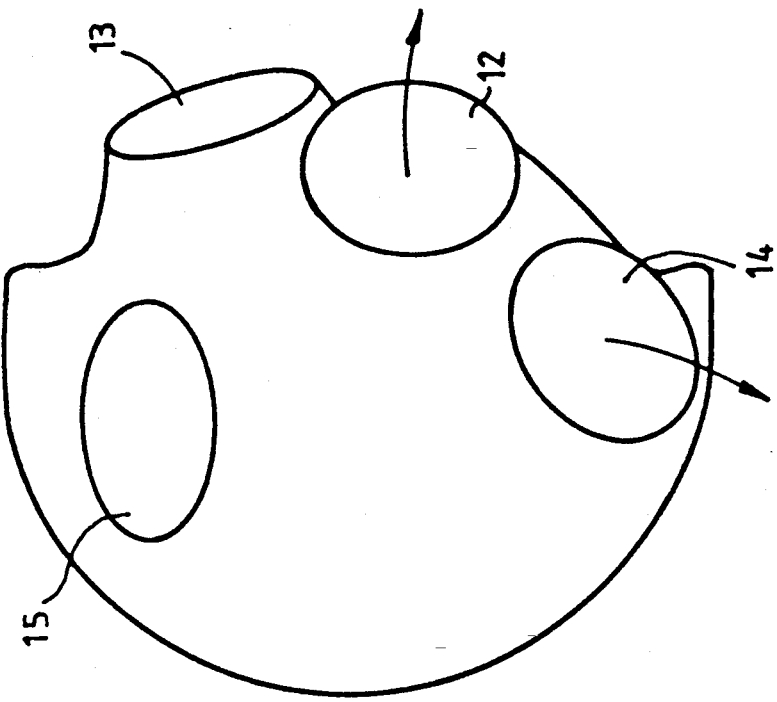
FIG. 9 is a schematic perspective view of the case of the prosthesis according to the invention comprising four valvular orifices.

Membrane 4 defines, with the internal face of the right-hand part of the case, which faces it, the right ventricle of the prosthesis, with a volume of about 250 cm$^3$ and in which a blood bag 19 is housed connected to the pulmonary and tricuspid valvular orifices 14 and 15, respectively, which are shown in FIG. 9, with valves not shown. In its rest condition, i.e. in the total absence of elongation, membrane 4 rests on a support part 5 formed by a thin rigid material web, e.g. made from metal or a reinforced or non reinforced plastic material, advantageously formed with holes 5a and whose shape is exactly that of membrane 4 which mates with it totally in its unstretched condition. As is clearly shown in FIGS. 1 and 5, membrane 4 at rest tends to have an ovoid shape, with relatively large radii of curvature in the top portion, in the drawing, i.e. towards the base of the prosthesis where the blood inlet 15 and outlet 14 orifices are provided and with smaller radii of curvature towards the tip of the prosthesis, in the bottom part in the drawing. This ovoid shape of the membrane combined with the shape of the internal face of the right-hand part of the wall of the case confers on the right ventricular cavity 17 a form which widens regularly in the three spatial dimensions, from the tip towards the base of the prosthesis.

Figure 7:
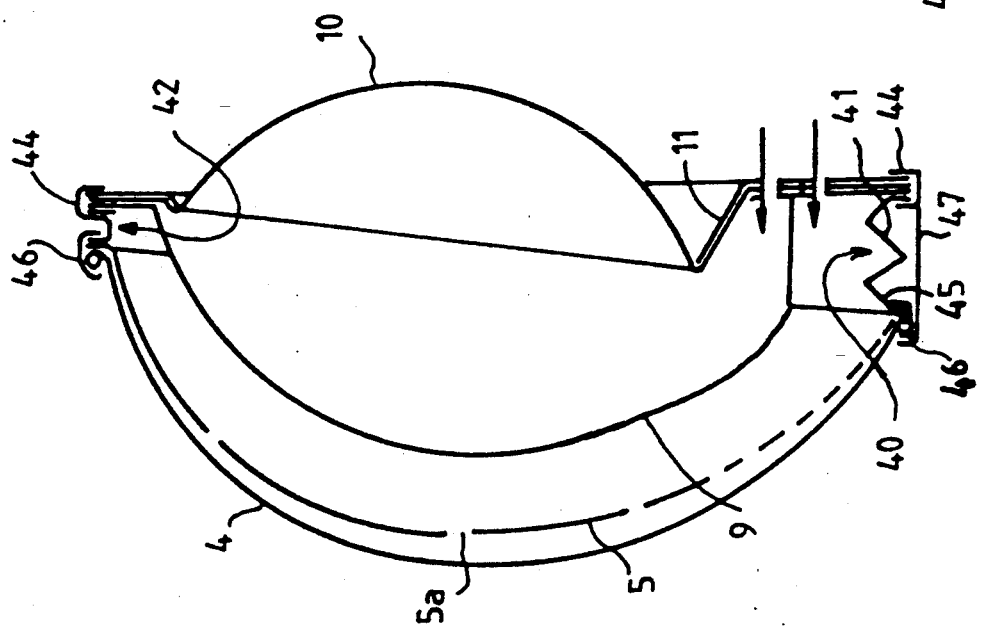
FIG. 7 is a schematic view of an improved prosthesis motor device in accordance with the invention.

The orifices 5a in the supporting web 5 whose density is greater in the tip portion than in the rest of said web, as shown schematically in FIG. 7 for example, are provided so as to permit the action on the membrane 4 of a pressurized fluid distributed by a pneumatic energy source connected to the prosthesis, known per se, whose inlet and outlet piping is shown at 16a for the right ventricle and at 16b for the left ventricle. The latter, referenced 18, occupies a volume substantially equal to that of the right ventricle and is limited by the internal face of the left-hand wall of the case 1, 2 and a dividing wall 9 which extends over the whole height of the prosthesis, from the tip to the base thereof.

The structure of the left ventricle, which is very close to that described in the above mentioned French patent FR-A-2 446 631, comprises as a drive member a thin membrane 10 which works under deformation (and not under elongation like membrane 4) on each side of a plane B—B slanted with respect to the longitudinal axial plane of the prosthesis. Membrane 10 is fixed laterally to a rigid material support 11, made for example from stainless steel, which limits its deformation so as to prevent complete crushing, in the systole phase, of a blood bag 20 housed in the ventricular space 18 and which has, towards the base of the prosthesis, the blood inlets and outlets corresponding to the valvular orifices 12 and 13 of the case, namely the aortic and mitral orifices, respectively. The left ventricular space 18 also has a shape progressively increasing in the three spatial dimensions, from the tip towards the base of the prosthesis, such an arrangement promoting laminar flow without turbulence and eliminating the zero speed zones in said space while favorably orienting the speed vectors of the blood moving toward the aorta.

According to the invention, membrane 4 of the right ventricle and the support part 5 associated therewith are not fixed rigidly to the case of the prosthesis, as in the prior known construction, but are fixed at their periphery to an end flange of a bellows whose other end flange is immobilized with respect to the case and/or the longitudinal dividing wall 9 separating, from the pneumatic energy point of view, the right ventricle from the left ventricle.

In a first embodiment, bellows 30 is, in accordance with the invention, FIGS. 1 to 4, made from an elastic material, e.g. an elastomer (natural rubber or neoprene) and of the type with parallel displacement, namely adapted so that its turns 31—compressed at the systole beginning (FIGS. 1 and 3)—are moved apart from each other over the whole of the periphery of the bellows at the end of systole (FIGS. 2 and 4). More precisely, one of the end flanges 32 of bellows 30 is crimped by a ring 33 on the dividing wall 9, the membrane 10 and its support 11 whereas its other end flange 34 is crimped to a ring or annulus 35 on the entire periphery of the membrane 4 and support part 5.

Abutment stirrups 36, fixed to ring 33 and advantageously disposed in the case 1, 2 of the prosthesis, on each side of the plane of symmetry of said case, have at their ends distant from flange 32 bends 37 with which the other end flange 34 of the bellows is adapted to cooperate for limiting the amplitude of its displacement during the systolic phase. At the beginning of the latter, the condition of the prosthesis is that shown in FIGS. 1 and 3; the introduction of pressurized fluid through pipe 16a first of all causes the membrane and the support part associated therewith 5 to move, with concomitant compressing of the blood bag 19, until flange 34 abuts against stops 37 then, from this position, an increase of the pressure of the drive fluid causes elongation of membrane 4 to finish the systolic phase of the right ventricle up to total emptying of the blood bag.

Breaking down the systole into two phases limits the elongation of membrane 4 to a value which may be about 7 to 10%, namely a value which does not induce in the material forming the membrane risks of microcracks or other defects likely to cause the destruction thereof for a number of operating cycles less than that anticipated. Despite the relatively low value of the elongation of membrane 4, the required volume of blood is expelled at each pulsation because of the initial compressing phase of the blood bag during the displacement of the bellows 30.

The motor device may be fed, from piping 16a and 16b, in phase or in phase opposition, the latter embodiment providing an energy module of smaller instantaneous power and further allowing the control pressures of the right ventricle and the left ventricle to be better regulated separately.

In a second embodiment, FIGS. 5 to 7, bellows 40 associated with membrane 4 and with its support part 5 of the right ventricle is of the pendular type and not the parallel displacement type as in the preceding embodiment. In this case it comprises turns 41 capable of moving away from each other in the zone of the tip of the right ventricle of the prosthesis and a hinge 42 opposite the tip of the prosthesis, i.e. in the base zone thereof. As in the preceding embodiment, an end flange 43 of the elastic bellows is crimped to dividing wall 9, membrane 10 and its support 11, by means of a ring 44 held in the pockets of case 1, 2 of the prosthesis, not shown, or by lugs 38, whereas the opposite end flange 45 is crimped, with membrane 4 and the support part 5 in a ring 46. Abutment stirrups 47 with arresting bends 48 with which flange 45 is adapted to cooperate, are here also fixed to ring 44 in the right ventricular space so as to limit the pendular movement of bellows 40. In such an embodiment, whose operation is otherwise similar to that described above, the presence of a hinge of the bellows at the base of the prosthesis causes, during the first phase of the systolic movement of the right ventricle, first of all emptying of the tip of the blood bag 19, which is the furthest away from the hinge, without substantially modifying at the same time the general shape of the ventricular space of the valvular zone during this first systolic phase. During the second phase, namely that which comprises elongation of membrane 4, the greater density of the perforations 5a of support part 5 towards the base of the prosthesis first of all deforms said membrane in its tip portion, with consequently speeding up of the blood contained in bag 19 from the tip to the base, favorable for the correct execution of the circulatory phenomenon. In both embodiments described above, the fixed end flange is advantageously crimped, as shown in FIG. 6a, namely in a ring 33 or 44 which simultaneously fixes the dividing wall 9, membrane 10 working under deformation and support 11 of said membrane in the portion 1, 2 of the case of the prosthesis, said case further comprising lugs 38 for holding said ring 33, 44 and/or stops 36, 47 by their ends laterally in position.

Figure 8:
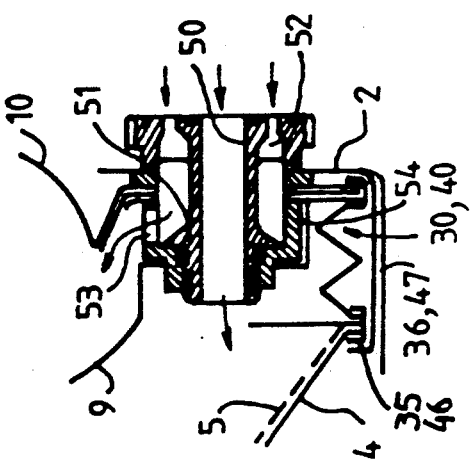
FIG. 8 is a detail view.

Whereas, in the two embodiments described above, pipes 16a and 16b connecting the motor device to the pressurized fluid source are disposed parallel to each other, it may be advantageous, in some embodiments, to provide concentric and not parallel connections. In such a construction, FIG. 8, it is the central bore 50 of a piece 51, placed at the tip of the prosthesis, which plays the role of pipe 16a, the role of pipe 16b being played by an annular chamber 52 surrounding bore 50 and which communicates through one or more passages 53 with the space defined by the dividing wall 9 and the membrane 10 working under deformation. In this embodiment, the parallel displacement bellows 30 or the pendular bellows 40 is disposed between part 2 of the case of the prosthesis and the external body 54 defining chamber 52, with mounting of the fixed and mobile flanges of said bellows similar to that described above.

What is claimed as new and desired to be secured by Letters Patent of the United States is:

1. A total heart prosthesis comprising:
a case implantable in the pericardial cavity and the geometry of which is very similar to that of the natural heart;
a motor device disposed inside the case, said motor device comprising first and second membranes, said first membrane working during an elongation stroke within a space defining the right ventricle and said second membrane working during a deformation stroke within a space defining the left ventricle;
blood bags enclosed in the right and left ventricular spaces, adapted to be connected to the vessels of the circulatory system of a patient by valves mounted in valvular orifices formed in the case of the prosthesis;
means for activating the motor device comprising a pneumatic energy source including servo loop means for regulating the blood flow, said activating means actuating said prosthesis;
wherein the first membrane and a movable support which is associated therewith are mounted in the case of the prosthesis by means for breaking down the movement of said first membrane into two phases, one of which is a displacement without elongation including displacement of said support and the other is accompanied only by an elongation whereas return movement of said first membrane comprises first a retraction phase followed by a displacement without modification of the shape of said first membrane and of the support associated therewith.

2. The total heart prosthesis as claimed in claim 1, wherein the means for breaking the movement of the first membrane down into two phases comprises at least one bellows adapted to be connected to the pneumatic energy source and one end of which the first membrane and the support associated therewith are fixed.

3. The total heart prosthesis as claimed in claim 2, wherein the bellows comprises a pendular displacement type bellows.

4. The total heart prosthesis as claimed in claim 3, wherein said prosthesis further comprises a base zone, a hinge mounting the bellows to the base zone of the prosthesis, where turns of the bellows are housed so that emptying of the blood bag of the right ventricle begins by a tip of said bag, thus promoting the circulatory process.

5. The total heart prosthesis as claimed in claim 2, further comprising said bellows being made from an elastic material having a first end to which the first membrane and the support associated therewith are fixed, and a second end fixed by crimping to a sealed dividing wall separating the right and left ventricular spaces of the prosthesis, on which dividing wall is also fixed the second membrane.

6. The total heart prosthesis as claimed in claim 2, further comprising stop means for limiting displacement of the end of the bellows to which said first membrane and the support are fixed during the elongation phase.

7. The total heart prosthesis as claimed in claim 6, wherein the stop means comprises stirrups limiting displacement of the bellows, said stirrups being fixed to a fixed ring, housed in the right ventricular space and provided with bends for arresting the end of the bellows.

8. The total heart prosthesis as claimed in claim 2, comprising a lubricant between the blood bags, the case of the prosthesis, the first and second membranes of the motor device and the means for breaking down the movement of said first membrane into two distinct phases.

9. The total heart prosthesis as claimed in claim 2, further comprising the bellows being immobilized by lugs attaching a first end flange of said bellows to the case of the prosthesis, said first end flange being crimped by means of a first ring cooperating with said lugs; and a second end flange of said bellows being crimped by a second ring on the first membrane working under elongation and on the support which is associated therewith.

10. The total heat prosthesis as claimed in claim 9, further comprising the pneumatic energy source connected to the motor device by a piece providing coaxial feeding of the right ventricle and the left ventricle, said piece being mounted to said case and located at a tip of the prosthesis.

11. The total heart prosthesis as claimed in any one of claims 1, 2, 3, 5, 6, 8 or 4, further comprising the support of the first membrane working under elongation of the right ventricle having a plurality of perforations with a greater density of perforations in a zone adjacent to a tip of the prosthesis than in the rest of said support.

* * * * *

UNITED STATES PATENT AND TRADEMARK OFFICE
CERTIFICATE OF CORRECTION

PATENT NO. : 5,089,018

DATED : February 18, 1992

INVENTOR(S) : Didier Lapeyre, et al.

It is certified that error appears in the above-identified patent and that said Letters Patent is hereby corrected as shown below: On the Title page, item [54], The title is incorrect, should be, -- TOTAL HEART PROSTHESIS--.

Signed and Sealed this

Fifteenth Day of June, 1993

Attest:

MICHAEL K. KIRK

*Attesting Officer*  *Acting Commissioner of Patents and Trademarks*